United States Patent [19]
Foote

[11] Patent Number: 5,830,157
[45] Date of Patent: Nov. 3, 1998

[54] GUIDEWIRE CONNECTION GUIDE AND METHOD OF USE

[75] Inventor: Jerrold L. Foote, Salt Lake City, Utah

[73] Assignee: Merit Medical Systems, Inc., South Jordan, Utah

[21] Appl. No.: 853,272

[22] Filed: May 9, 1997

[51] Int. Cl.$^6$ .................................................. A61B 5/00
[52] U.S. Cl. ................................................. 600/585
[58] Field of Search ................................ 600/434, 585

[56] References Cited

U.S. PATENT DOCUMENTS 5,651,373  7/1997  Mah ........................................ 600/585

*Primary Examiner*—Max Hindenburg
*Assistant Examiner*—Charles Marmor, II
*Attorney, Agent, or Firm*—Workman, Nydegger & Seeley

[57] ABSTRACT

A guidewire connection guide includes a back member having a top surface extending between opposing sidewalls. An open-topped channel is positioned on the top surface and extends linearly through and between each of the opposing sidewalls. A restraining member having a planar top surface is hingedly attached to the back member. The restraining member is selectively folded over to compress against the end of an extension guidewire positioned within the first end of the channel. An enclosing member also has a planar top surface and is hingedly connected to the back member adjacent to the restraining member. The enclosing member can be selectively biased against the top surface of the back member to cover a portion of the channel. The portion of the channel covered by the enclosing member defines a substantially enclosed alignment passageway. The alignment passageway has a first end with the end of the extension guidewire received therein and an opposing second end. The alignment passageway has a transverse cross section substantially complementary to the cross section of the guidewires. By positioning the tapered end of a guidewire within the second end of the alignment passageway, the guidewire can be selectively advanced therein so as to be self-guided into a coupling socket formed in the end of the extension guidewire.

22 Claims, 3 Drawing Sheets

GUIDEWIRE CONNECTION GUIDE AND METHOD OF USE

BACKGROUND OF THE INVENTION

1. The Field Of The Invention

The present invention relates to apparatus and methods for use in coupling a medical guidewire to an extension guidewire and, more specifically, to apparatus and methods for guiding the tapered end of a guidewire into a coupling socket formed at the end of an extension guidewire.

2. The Relevant Technology

Guidewires are long, slender, flexible wires used for the intervascular placement of catheters. Conventional catheters are elongated, pliable tubes having opposing ends with a passageway longitudinally extending therebetween. Catheters come in a variety of different sizes, shapes, and designs to perform alternative functions. For example, catheters can be implanted within the body of a patient to accurately deliver medication to a predetermined location within the body. Alternatively, catheters can be configured to radially expand like a balloon within a vein to open a clogged vein.

In one method for implanting a catheter within the body of a patient, the guidewire is initially fed through the passageway in the catheter until the tip of the guidewire projects slightly past the tip of the catheter. Next, the tip of the catheter having the guidewire projecting therefrom is inserted through an incision into a vein. By pinching the guidewire between the pliable walls of the catheter, the guidewire and catheter can simultaneously be advanced within the vein.

Although guidewires are flexible along their length, they are relatively resistant to torsional or rotational bending. Accordingly, by rotating the free proximal end of the guidewire, the tip or distal end of the guidewire positioned within the vein can be selectively oriented to face a desired direction. A surgeon viewing the inserted catheter and guidewire through an x-ray machine is thus able to direct the guidewire and catheter through the maze of interconnected veins until the catheter is positioned at a desired location.

A variety of different sizes and kinds of catheters are often required during a single operation. To minimize the time and effort required to place each of the catheters, it is preferable that the guidewire be left in place while the original catheter is slid back and off the guidewire. The new catheter can then simply be slid over the exposed proximal end of the guidewire and advanced along the guidewire until appropriately positioned.

The problem with this method is that it is difficult to pull the catheter out of the patient without moving the guidewire. In one approach to solving this problem, the guidewire has a length greater than twice that of the catheter. The extended length of the guidewire enables the exposed proximal end of the guidewire to be held in place while the catheter is slid back over the guidewire and out of the patient. The problem with this approach is that guidewires of such extended length are extremely awkward to work with, especially during manipulation of the guidewire for implanting the catheter.

In an alternative approach, an extension guidewire is selectively coupled to the proximal end of the guidewire just prior to removal of the catheter. The extension guidewire effectively increases the length of the guidewire allowing removal of the catheter in the same manner as described above. The attachment of an extension guidewire, however, creates its own problems. For example, the joint between the guidewire and the extension guidewire must be almost seamless. This enables the surgeon to have adequate "feel" of the catheter during insertion over the guidewire and also prevents the guidewire from damaging the internal surface of the catheter. One approach to coupling the guidewire to the extension guidewire is to taper the proximal end of the guidewire and form a complementary coupling socket at the distal end of the extension guidewire. By inserting the proximal end of the guidewire into the coupling socket, a smooth, secure coupling is made between the guidewire and the extension guidewire.

The primary obstacle in using an extension guidewire is the difficulty in inserting the proximal end of the guidewire into the coupling socket of the extension guidewire. Guidewires must be small enough to fit within a catheter which in turn must be small enough to fit within a vein. Accordingly, guidewires have an extremely small diameter ranging from about 0.01 inches to about 0.02 inches. The diameter is further decreased at the tapered end of the guidewire, thereby making it difficult, even for the most stable of hands, to manually direct the proximal end of the guidewire into the correspondingly small coupling socket. During surgery, the difficulty of this process is further exacerbated by the fact that the operating room is typically dark to better enable the surgeon to view the monitor used in implanting the guidewire and catheter. Furthermore, the pressures and urgency often found in an operating room make it difficult to perform the intricate coupling quickly.

OBJECTS AND BRIEF SUMMARY OF THE INVENTION

It is therefore an object of the present invention to provide improved methods and apparatus for guiding the end of a guidewire into the coupling socket of an extension guidewire.

Another object of the present invention is to provide methods and apparatus as above in which the end of the guidewire is self-guided into the coupling socket.

Yet another object of the present invention is to provide the above methods and apparatus wherein the proximal end of the guidewire can be easily and quickly guided into the coupling socket of the extension guidewire under conditions commonly found in an operating room.

To achieve the foregoing objects, and in accordance with the invention as embodied and broadly described herein. A guidewire connection guide is provided for guiding the tapered proximal end of a guidewire into a coupling socket formed at one end of an extension guidewire. The guidewire connection guide includes a back member having a top surface extending between opposing sidewalls. An open-topped channel is recessed into the top surface and longitudinally extends between and through each of the opposing sidewalls. Hingedly mounted to the back member is a restraining member having a substantially planar top surface. During use of the guidewire connection guide, the end of the extension guidewire having a coupling socket formed therein is positioned within the end of the channel adjacent to the restraining member. The restraining member is then folded over such that the top surface thereof compress the end of the extension guidewire within the channel, thereby securing the end of the extension guidewire within the channel.

The guidewire connection guide also includes an enclosing member that is hingedly mounted to the back member adjacent to the restraining member. The enclosing member has a top planar surface configured to selectively bias against the top surface of the back member so as to cover a portion of the channel. The portion of the channel covered by the enclosing member defines an alignment passageway having openings formed at the opposing sidewalls of the enclosing member.

The extension guidewire is initially positioned within the channel such that the opening to the coupling socket is positioned within the first end of the alignment passageway. The alignment passageway has a transverse cross section that is substantially complementary to the cross section of both the guidewire and extension guidewire. The tapered proximal end of the guidewire is selectively positioned within the opposing second end of the alignment passageway. By advancing the guidewire within the alignment passageway, the guidewire is self-guided into the coupling socket of the extension guidewire. The connected wires can then be removed from the guidewire connection guide by simply folding back the restraining member and the enclosing member. The guidewire extension guide thus provides a quick, easy, and effective way for self-guiding the tapered end of a guidewire into the coupling socket of an extension guidewire.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
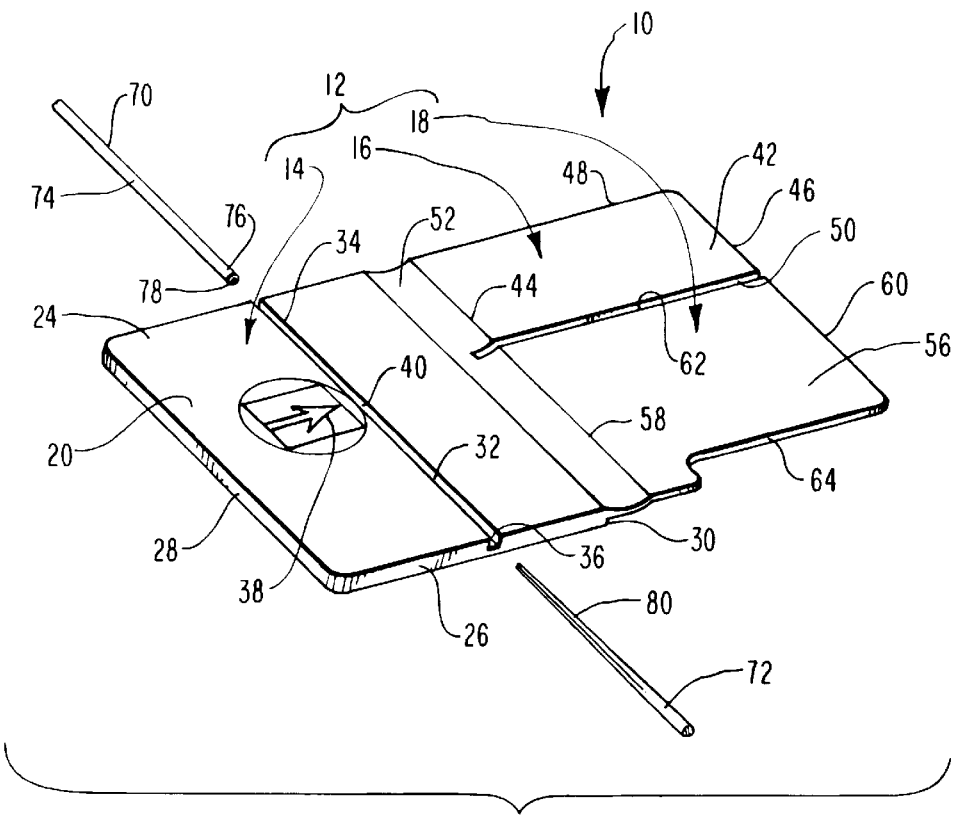
FIG. 1 is a perspective view of one embodiment of a guidewire connection guide incorporating features of the present invention.
Figure 2:
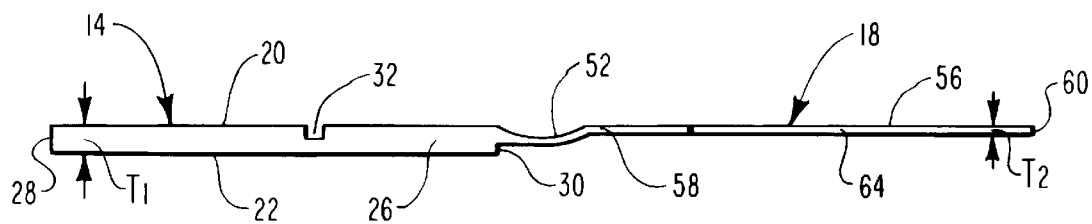
FIG. 2 is an elevated side view of the guidewire connection guide shown in FIG. 1.

Depicted in FIG. 1 is one embodiment of a guidewire connection guide 10 incorporating features of the present invention. Guidewire connection guide 10 comprises a body 12 including a back member 14, a restraining member 16, and an enclosing member 18. Depicted in FIGS. I and 2, back member 14 has a low profile box shaped configuration defined by a top surface 20, a bottom surface 22, opposing sidewalls 24 and 26, and opposing end walls 28 and 30.

Extending longitudinally between sidewalls 24 and 26 on top surface 20 is an open-topped channel 32. Channel 32 has a first end 34 that extends through sidewall 24 and an opposing second end 36 that extends through sidewall 26. Although channel 32 is depicted as having a substantially square transverse cross-section, in alternative embodiments, channel 32 can have virtually any transverse cross-sectional shape in which a guidewire can be received therein. For example, channel 32 can have a transverse cross-section that is semicircular, triangular, or polygonal. As will be discussed later in greater detail, positioned on top surface 20 is an indicator 38 defining a positioning point 40 along alignment channel 32.

Restraining member 16 comprises a planar top surface 42 that extends between opposing end walls 44 and 46 and opposing sidewalls 48 and 50. End wall 44 of restraining member 16 is connected to endwall 30 of back member 14 by a living hinge 52. Living hinge 52 enables restraining member 16 to repeatedly and selectively fold over to bias against back member 14. More specifically, top surface 42 of restraining member 16 can be selectively biased against top surface 20 of back member 14 such that restraining member 16 covers first end 34 of alignment channel 32.

Enclosing member 18 is adjacently positioned in parallel alignment with restraining member 16. Enclosing member 18 comprises a planar top surface 56 that extends between opposing end walls 58 and 60 and opposing sidewalls 62 and 64. Endwall 58 is connected to endwall 30 of back member 14 by living hinge 52. Living hinge 52 enables enclosing member 18 to repeatedly and selectively fold over to bias against back member 14. More specifically, top surface 56 of enclosing member 18 can be selectively biased against top surface 20 of back member 14 to substantially cover second end 36 of alignment channel 32.

Guidewire connection guide 10 is integrally molded from a plastic and, more preferably, a high density polypropylene. These materials not only enable guide 10 to be manufactured inexpensively and quickly but also give extended life to hinge 52. For reasons that will be discussed later in greater detail, it is preferred in one embodiment that restraining member 16 and enclosing member 18 be relatively flexible while back member 14 be relatively stiff. Where polypropylene is used, the flexibility of the elements can be regulated by modifying their thickness. For example, in one embodiment, back member 14 has a thickness $T_1$. in a range between about 0.04 inches to about 0.05 inches. In contrast, restraining member 16 and enclosing member 18 each have a thickness $T_2$ in a range between about 0.02 inches to about 0.03 inches. In alternative embodiments, guidewire connection guide 10 can be formed from a variety of different materials such as metals, ceramics, or composites. In yet another embodiment, discrete elements of guidewire connection guide 10 can be made of different materials. Furthermore, the elements of guidewire connection guide 10 can be discretely connected rather than integrally molded.

Guidewire connection guide 10 is used in selectively coupling an extension guidewire 70 to a guidewire 72. Extension guidewire 70 has an end 74 which terminates at a tip 76. Recessed longitudinally within tip 76 is a tubular coupling socket 78. Guidewire 72 has a tapered end 80 configured to be received within coupling socket 78.

Figure 3:
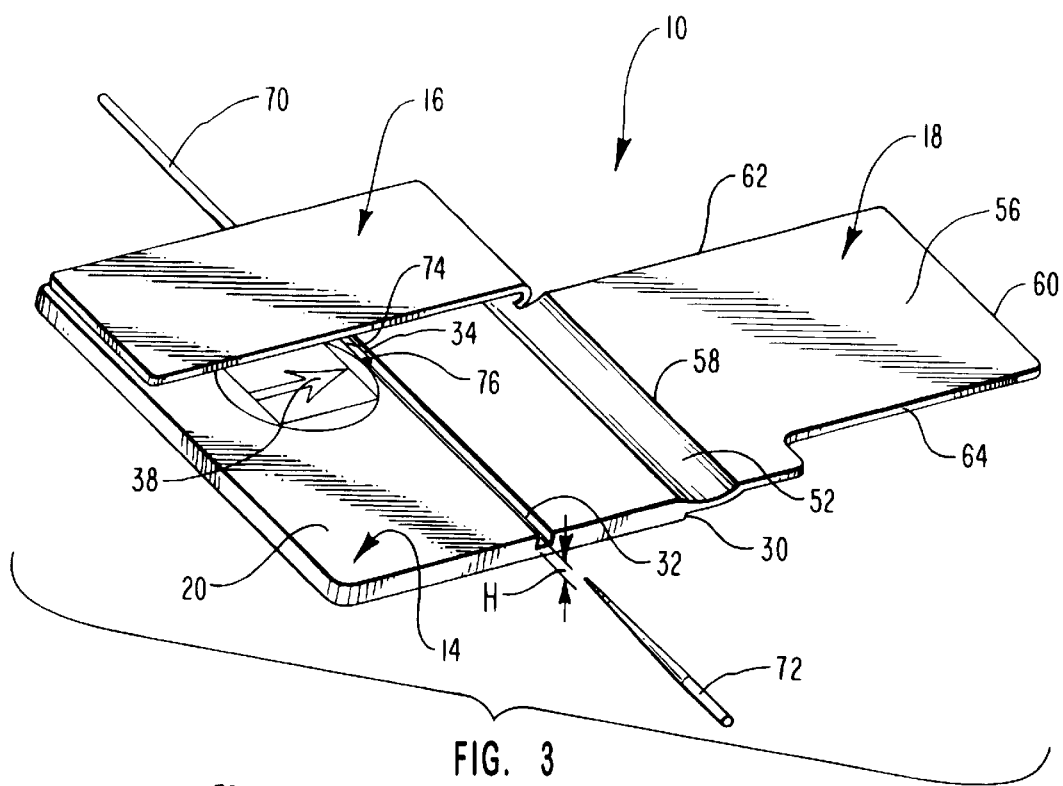
FIG. 3 is a perspective view of the guidewire connection guide shown in FIG. 1 with the restraining member thereof folded over.

During use of guidewire connection guide 10, end 74 of extension guidewire 70 is initially disposed within first end 34 of channel 32 such that tip 76 is aligned with indicator 38 as depicted in FIG. 3. Restraining member 16 is then folded over and biased against back member 14. Channel 32 has a height H that is substantially similar to, or slightly smaller than, the diameter of extension guidewire 70 and guidewire 72. Restraining member 16 thus compresses end 74 of extension guidewire 70 with channel 32, thereby securely holding extension guidewire 70 within channel 32.

As height H of channel 32 increases relative to the diameter of extension guidewire 70, the flexibility of restraining member 16 should be increased. The increased flexibility enables restraining member 16 to compress against extension guidewire 70 within channel 32. In contrast, where the diameter of extension guidewire 70 is greater than height H of channel 32, extension guidewire 70 will project above top surface 20 of back 14. As a result, restraining member 16 requires minimal flexibility to bias against extension guidewire 70.

The present invention includes means for securing the end of a first guidewire within channel 32. By way of example and not by limitation, one embodiment for the means for securing includes restraining member 16, as discussed above. In alternative embodiments, restraining member 16 can be a discrete element that is not connected to back member 14. Furthermore, restraining member 16 can be formed with a ridge projecting from top surface 42. The ridge would be positioned to selectively be received within channel 32 when restraining member 16 is biased against back member 14. In this way, the ridge would directly bias against extension guidewire 70 positioned within channel 32. Although restraining member 16 in FIG. 1 is shown having a flat planar configuration, in alternative embodiments of the means for securing the end of the guidewire, restraining member 16 can have virtually any configuration as long as it has one side capable of compressing the guidewire positioned within channel 32.

Figure 4:
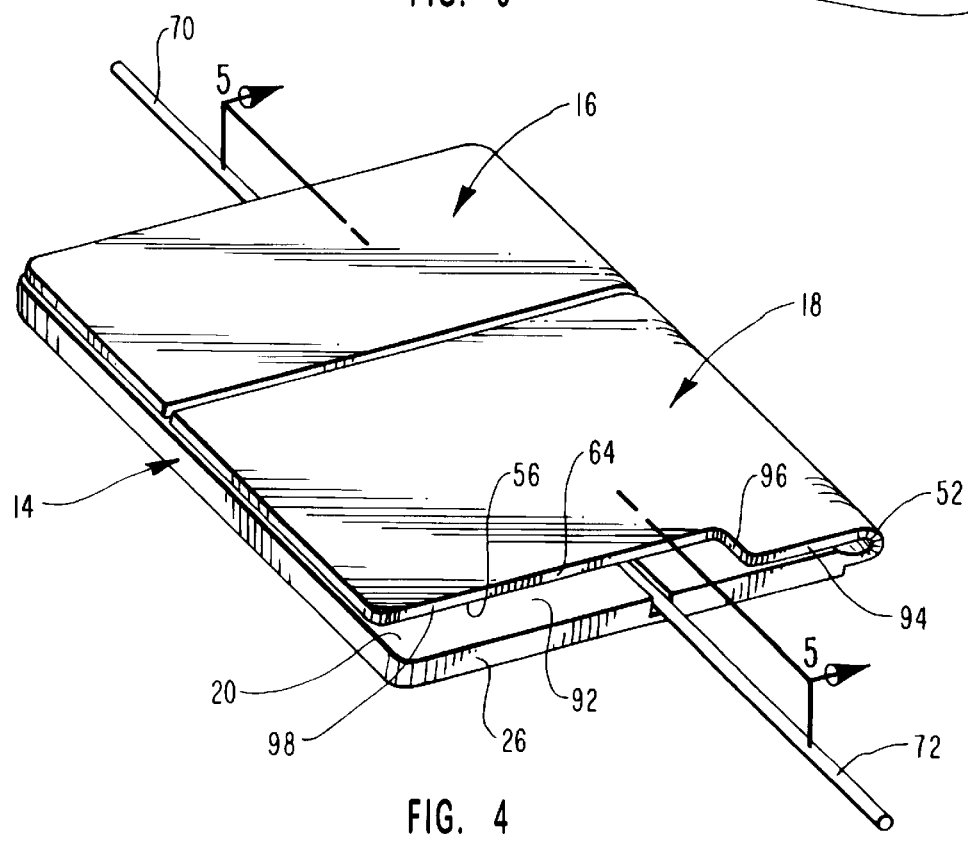
FIG. 4 is a perspective view of the guidewire connection guide shown in FIG. 3 with the enclosing member thereof folded over.
Figure 5:
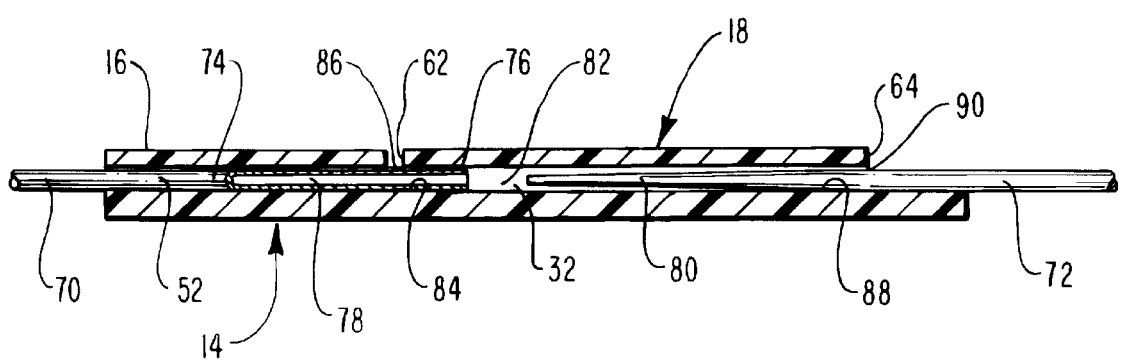
FIG. 5 is a cross-sectional side view of the guidewire connection guide shown in FIG. 4 taken along section line 5—5.

Enclosing member 18, as shown in FIG. 4, is next folded over such that top surface 56 of enclosing member 18 is biased against top surface 20 of back member 14. As depicted in FIG. 5, the portion of channel 32 covered by enclosing member 18 defines a substantially enclosed alignment passageway 82. Alignment passageway 82 has a first end 84 with an opening 86 communicating therewith at sidewall 62 of enclosing member 18. Alignment passageway also has a second end 88 with an opening 90 communicating therewith at sidewall 64 of enclosing member 18.

Indicator 38 is positioned such that tip 76 of extension guidewire 70 is positioned within first end 84 of alignment passageway 82 when enclosing member 18 is folded over. End 80 of guidewire 72 is next received within second end 88 of alignment passageway 82 and advanced therein.

Alignment passageway 82 has a transverse cross section that is substantially complementary to the transverse cross section of guidewire 72. That is, although the cross section of the alignment passageway 82 may be slightly smaller than or slightly larger than the cross section of guidewire 72, the cross sections are substantially close enough that as guidewire 72 is advanced within alignment passageway 82, alignment passageway 82 acts as a guide to direct tapered end 80 of guidewire 72 into coupling socket 78 of extension guidewire 70.

The present invention also includes means for covering channel 32 having the end of a first guidewire received therein such that the end of a second guidewire can be received and self-guided within the covered channel to effect insertion of the end of one of the guidewires into a coupling socket of the other guidewire. One embodiment of the means for covering includes enclosing member 18, as disclosed above. In alternative embodiments, the covering means encompasses enclosing member 18 in a variety of alternative shapes and sizes. For example, enclosing member 18 may have a ridge projecting from top surface 56 which is complementarily received in channel 32. Alternatively, a grooved channel may be formed on top surface 56 that is complementarily aligned with channel 32 for forming alignment passageway 82. In yet other embodiments, enclosing member 18 can comprise a plurality of discrete elements that bias together to cover channel 32. Finally, enclosing member 18 need not be directly connected to back member 14 or may be connected thereto using a variety of alternative hinge or latching structures.

The present invention also includes means for guiding the end of a guidewire 72 into second end 88 of alignment passageway 82. By way of example and not by limitation, as depicted in FIG. 4, sidewall 64 of enclosing member 18 defines a notched recess 92. More specifically, sidewall 64 comprises a first sidewall portion 94 that extends from hinge 52 parallel with sidewall 26 of back member 14, a second sidewall portion 98 positioned parallel to and spaced back from first sidewall portion 94, and a blocking shoulder 96 extending substantially parallel with channel 32 between first sidewall portion 94 and second sidewall portion 98.

Notched recess 92 enables end 80 of guidewire 72 to be positioned on top surface 20 of back member 14. Using second sidewall portion 98 and blocking shoulder 96 as a guide, guidewire 72 can be horizontally moved along top surface 20 until end 80 of guidewire 72 falls into channel 32. In alternative embodiments to the means for guiding, blocking shoulder 96 can be positioned directly adjacent to channel 32 for better defining the location of channel 32. In yet other alternative embodiments, a variety of conventional shapes can be used for directing end 80 of guidewire 72 into channel 32. For example, enclosing member 18 and back member 14 can each have complementary halves of a funnel positioned thereon. As the two members are pressed together, the corresponding halves of the funnel are complementarily aligned forming a complete funnel that communicates with alignment passageway 82. The funnel could then be used for directing end 80 of guidewire 72 into alignment passageway 82.

The coupled guidewire 72 and extension guidewire 70 can be removed from guidewire connection guide 10 by simply folding back restricting member 16 and enclosing member 18 so as to open channel 32.

FIGS. 1–5 show the connection of extension guidewire 70 to guidewire 72 by initially positioning end 74 of extension guidewire 70 into first end 34 of channel 32. In alternative uses, guidewire connection guide 10 can also be used by first inserting tapered end 80 of guidewire 72 in first end 34 of channel 32.

Restraining member 16 is useful in the present invention in that it enables extension guidewire 70 to be securely held to guidewire connection guide 10 for subsequent connection with guidewire 72. In alternative embodiments, however, restraining member 16 can be eliminated. In this embodiment, enclosing member 18 also performs the function of restraining member 16. That is, once end 74 of extension guidewire 70 is received within first end 84 of alignment passageway 82, enclosing member 18 overlying extension guidewire 70 can be used to compress extension guidewire 70 within channel 32. Guidewire 72 can then be received within second end 88 of alignment passageway 82 for insertion into coupling socket 78, as discussed above.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by united states letters patent is:

1. An apparatus for selectively coupling a first guidewire to a second guidewire, wherein the first guidewire has a coupling socket formed in a proximal end thereof and the second guidewire has complimentary tapered end formed in a distal end thereof, the apparatus comprising:

a back member with an elongated alignment channel formed therein and extending the entire width of the back member, the elongated channel being configured to receive a portion of the first guidewire and a portion of the second guidewire in axial alignment; and means selectively positionable over a first portion of said channel containing the coupling socket of the first guidewire, for selectively securing the first guidewire in a fixed position relative to the back member while the tapered end of the second guidewire is advanced into and coupled with the coupling socket of the first guidewire; and means selectively positionable over a second portion of said channel containing the tapered end of the second guidewire for covering the second channel portion such that the complimentary tapered end of the second guidewire can be received and self-guided within the second covered channel portion to effect insertion of the complimentary tapered end of the second guidewire into the coupling socket of the first guidewire.

2. An apparatus as recited in claim 1, wherein the means for selectively securing comprises a retaining member hingedly mounted to the back member so as to selectively fold over and bias against the first guidewire within the alignment channel.

3. An apparatus as recited in claim 1, wherein the means for covering the second channel portion comprises an enclosing member having a substantially planar surface configured to span over the channel having the end of the first guidewire received therein, thereby forming a substantially longitudinally enclosed alignment passageway.

4. An apparatus as recited in claim 3, wherein the alignment passageway has a first end, an opposing second end, and openings formed thereat, the transverse cross section of the alignment passageway being substantially complementary to the cross section of each of the guidewires.

5. An apparatus as recited in claim 3, wherein the enclosing member is hingedly mounted to the back member.

6. An apparatus as recited in claim 1, wherein the channel has a substantially square transverse cross section.

7. An apparatus as recited in claim 1, further comprising means for securing the end of the first guidewire within the channel prior to covering the end of the first guidewire within the channel.

8. An apparatus as recited in claim 7, wherein the means for securing the end of the first guidewire comprises a retaining member configured to cover a longitudinal portion of the channel having the first guidewire received therein when the retaining member is biased against the back member.

9. An apparatus as recited in claim 8, wherein the retaining member is hingedly connected to the back member.

10. An apparatus for selectively coupling a first guidewire to a second guidewire by inserting the end of one of the guidewires into a coupling socket positioned at an end of the other guidewire, the apparatus comprising:

a back member having a top surface with an open-topped channel formed thereon, the channel having opposing first and second ends and being configured to receive a guidewire;

an enclosing member hingedly mounted to the back member, the enclosing member being configured to selectively cover at least a portion of the channel when the end of the first guidewire is positioned within the first end of the channel;

an opening communicating with the covered channel at the second end thereof, the opening enabling the end of the second guidewire to be selectively advanced into the channel covered by the enclosing member such that the end of one or the guidewires is self-guided into the coupling socket of the other guidewire and means for guiding the end of the second guidewire into the open of the channel covered by the enclosing member, and wherein the means for guiding the end of the second guidewire into the opening comprises a notched recess formed on the cover member adjacent to the second end of the alignment channel.

11. An apparatus as recited in claim 10, further comprising a retaining member hingedly connected to the back member, the retaining member being configured to selectively bias against the first guidewire when the first guidewire is received within the alignment channel.

12. An apparatus as recited in claim 10, wherein the back member and the cover member are integrally molded together.

13. An apparatus as recited in claim 10, wherein the back member comprises:

(a) a pair of opposing side walls with the, top surface extending therebetween; and (b) the channel extending between and through each of the opposing side walls.

14. An apparatus as recited in claim 10, wherein the channel has a width in a range between about 0.01 inches and about 0.02 inches.

15. A guidewire assembly kit comprising (a) an elongated, flexible guidewire having a proximal tip and a distal end;

(b) an elongated, flexible extension guidewire having an attachment end with a coupling socket positioned thereat, the coupling socket being configured to receive the distal end of the guidewire; and (c) a guidewire connecting guide comprising:

(i) a back member comprising a top surface extending between opposing first and second sidewalls and an open-topped channel extending on the top surface through and between each of the opposing first and second sidewalls, the channel being configured to receive the distal end of the guidewire and the attachment end of the extension guidewire in longitudinal alignment;

(ii) a securing means having a substantially planar top surface, the securing means being hingedly connected to the back member to selectively cover a longitudinal portion of the channel when top surface of the securing means is biased against the top surface of back member; and (iii) a enclosing member having a substantially planar top surface, the enclosing member being hingedly connected to the back member to selectively cover a longitudinal portion of the channel adjacent to the portion of the channel covered by the restraining member when the top surface of the enclosing member is biased against the top surface of the back member; and (iv) a notched recess; formed on the enclosing member adjacent to the second sidewall of the base member.

16. A guidewire assembly kit as recited in claim 15, wherein the channel has a substantially square transverse cross section.

17. A guidewire assembly kit as recited in claim 15, wherein the channel has a transverse width complementary to the diameter of the guidewire.

18. A guidewire assembly kit as recited in claim 15, wherein the guidewire connecting guide is integrally molded from polypropylene plastic.

19. A method for selectively coupling a first guidewire to a second guidewire by inserting the end of one of the guidewires into a coupling socket positioned at an end of the other guidewire, the method comprising the steps of positioning the end of the first guidewire within a first end of an open-topped channel formed on a guidewire connecting guide;

covering at least a portion of the channel with a first portion of an enclosing member to form an enclosed alignment passageway having a first end and a second end, the end of the first guidewire being disposed within the first end of the alignment channel;

enclosing with a second portion of the enclosing member the second end of the alignment channel, inserting the end of the second guidewire within the second end of the alignment passageway; and advancing the second guidewire within the alignment channel such that the end of one of the guidewires is guided into the coupling socket at the end of the other guidewire.

20. A method as recited in claim 19, further comprising the step of biasing a restraining member against the first guidewire positioned within the channel prior to the step of covering.

21. A method as recited in claim 19, wherein the first guidewire comprises an extension guidewire having the coupling socket positioned at the end thereof.

22. A method as recited in claim 19, wherein the second guidewire comprises an extension guidewire having the coupling socket positioned at the end thereof.

\* \* \* \* \*

UNITED STATES PATENT AND TRADEMARK OFFICE
CERTIFICATE OF CORRECTION

PATENT NO. : 5,830,157

DATED : November 3, 1998

INVENTOR(S) : Jerrold L. Foote

It is certified that error appears in the above-identified patent and that said Letters Patent is hereby corrected as shown below:

Col. 1, ln. 14: before "placement" change "intervascular" to --intravascular--

Col. 7, ln. 27: after "the" and before "tapered" insert --complimentary--

Col. 7, ln. 55: after "the" and before "end" insert --proximal--

Col. 7, ln. 56: after "the" and before "end" insert --proximal--

Col. 8, ln. 35: after "the" and before "top" delete [,]

Col. 8, ln. 61: after "when" and before "top" insert --the--

Col. 8, ln. 63: after "of" and before "back" insert --the--

Col. 8, ln. 64: after "(iii)" change "a" to --an--

Col. 9, ln.1-2: after "by the" change "restraining member" to --securing means--

Col. 9, ln. 5: after "recess" and before "formed" delete [;]

UNITED STATES PATENT AND TRADEMARK OFFICE
CERTIFICATE OF CORRECTION

PATENT NO. : 5,830,157
DATED : November 3, 1998
INVENTOR(S) : Jerrold L. Foote

It is certified that error appears in the above-identified patent and that said Letters Patent is hereby corrected as shown below:

Col. 9, ln. 6: after "of the " change "base" to --back--

Col. 9, ln. 19: after "steps of" insert --:--

Col. 10, ln. 5: after "channel," insert paragraph break

Signed and Sealed this

Third Day of October, 2000

*Attest:*

Q. TODD DICKINSON

*Attesting Officer*  *Director of Patents and Trademarks*